US009700546B2

(12) United States Patent
Chien et al.

(10) Patent No.: US 9,700,546 B2
(45) Date of Patent: Jul. 11, 2017

(54) TRIVALENT CHROMIUM COMPOUNDS, COMPOSITIONS AND METHODS OF USE

(71) Applicant: INTERHEALTH NUTRACEUTICALS, INC., Benicia, CA (US)

(72) Inventors: Xiaoming X. Chien, San Ramon, CA (US); Debasis Bagchi, Concord, CA (US)

(73) Assignee: INTERHEALTH NUTRACEUTICALS, INC., Benicia, CA (US)

( * ) Notice: Subject to any disclaimer, the term of this patent is extended or adjusted under 35 U.S.C. 154(b) by 97 days.

(21) Appl. No.: 14/793,657

(22) Filed: Jul. 7, 2015

(65) Prior Publication Data

US 2015/0306083 A1 Oct. 29, 2015
US 2016/0354353 A9 Dec. 8, 2016

Related U.S. Application Data

(60) Division of application No. 12/251,310, filed on Oct. 4, 2008, now abandoned, which is a continuation-in-part of application No. PCT/US2007/066544, filed on Apr. 12, 2007.

(60) Provisional application No. 60/791,286, filed on Apr. 12, 2006.

(51) Int. Cl.
*A61K 31/28* (2006.01)
*A61K 31/4406* (2006.01)
*A61K 33/24* (2006.01)
*A61K 36/185* (2006.01)
*A61K 36/22* (2006.01)
*A61K 36/38* (2006.01)
*A61K 36/49* (2006.01)
*A61K 36/54* (2006.01)
*A61K 36/82* (2006.01)
*C07C 57/44* (2006.01)
*C07C 59/285* (2006.01)
*C07C 65/03* (2006.01)
*C07C 229/76* (2006.01)

(52) U.S. Cl.
CPC .......... *A61K 31/4406* (2013.01); *A61K 31/28* (2013.01); *A61K 33/24* (2013.01); *A61K 36/185* (2013.01); *A61K 36/22* (2013.01); *A61K 36/38* (2013.01); *A61K 36/49* (2013.01); *A61K 36/54* (2013.01); *A61K 36/82* (2013.01); *C07C 57/44* (2013.01); *C07C 59/285* (2013.01); *C07C 65/03* (2013.01); *C07C 229/76* (2013.01)

(58) Field of Classification Search
CPC .... A61K 31/28; A61K 31/4406; A61K 33/24; A61K 36/185; A61K 36/22; A61K 36/38; A61K 36/49; A61K 36/54; A61K 36/82; C07C 229/76; C07C 57/44; C07C 59/285; C07C 65/03
See application file for complete search history.

(56) References Cited

U.S. PATENT DOCUMENTS

| | | | |
|---|---|---|---|
| 3,925,433 | A | 12/1975 | Abdel-Monem et al. |
| 4,096,093 | A | 6/1978 | Hwang |
| 4,150,208 | A | 4/1979 | Hwang |
| 4,405,501 | A | 9/1983 | Witt |
| 4,436,882 | A | 3/1984 | Witt |
| 4,923,855 | A | 5/1990 | Jensen |
| 4,954,492 | A | 9/1990 | Jensen |
| 5,194,615 | A | 3/1993 | Jensen |
| 5,266,560 | A | 11/1993 | Furman et al. |
| 5,536,838 | A | 7/1996 | Wong |
| 5,614,224 | A | 3/1997 | Womack |
| 5,730,988 | A | 3/1998 | Womack |
| 6,447,809 | B1 | 9/2002 | Krumhar et al. |
| 6,689,383 | B1 | 2/2004 | Anderson et al. |
| 7,029,703 | B2 | 4/2006 | Krumhar et al. |
| 7,247,328 | B2 | 7/2007 | Abdel-Monem et al. |
| 7,271,278 | B2 | 9/2007 | Sreejayan et al. |
| 2003/0143311 | A1 | 7/2003 | Gillota |
| 2004/0106591 | A1 | 6/2004 | Pacioretty et al. |
| 2005/0239750 | A1 | 10/2005 | Motyka et al. |
| 2005/0239763 | A1 | 10/2005 | Motyka et al. |
| 2007/0134300 | A1 | 6/2007 | Abdel-Monem et al. |
| 2008/0003303 | A1 | 1/2008 | Chien et al. |
| 2008/0114065 | A1 | 5/2008 | Pacioretty et al. |

FOREIGN PATENT DOCUMENTS

| | | |
|---|---|---|
| CN | 1161801 A | 10/1997 |
| CN | 1218054 A | 6/1999 |
| CN | 1252273 A | 5/2000 |
| CN | 1308955 A | 8/2001 |
| CN | 1342456 A | 4/2002 |
| CN | 1709907 A | 12/2005 |
| WO | WO-8910357 A1 | 11/1989 |

(Continued)

OTHER PUBLICATIONS

Atkinson et. al., The Lancet, 2001, Williams and Wilkins, vol. 358, pp. 221-229.*
Pollock, Seminars in Avian and Exotic Pet Medicine, 2002, W.B. Saunders & Co., vol. 11(2), pp. 57-64.*
International Search Report from corresponding PCT/US2007/066544 dated Mar. 26, 2008.
Written Opinion from corresponding PCT/US2007/066544.
International Preliminary Report on Patentability from corresponding PCT/US2007/066544 dated Oct. 14, 2008.
Anderson et al., "Dietary Chromium Effects on Tissue Chromium Concentrations and Chromium Absorption in Rats," *The Journal of Trace Elements in Experimental Medicine* 9 :11-25 (1996).

(Continued)

*Primary Examiner* — Sarah Pihonak
(74) *Attorney, Agent, or Firm* — Marshall, Gerstein & Borun LLP

(57) ABSTRACT

The present invention provides chromium compounds, specifically chromium dinicocysteinate, which possess the ability to improve insulin sensitization, glucose tolerance, bioavailability, efficacy, and safety, and methods for their use.

15 Claims, No Drawings

(56) References Cited

FOREIGN PATENT DOCUMENTS

| WO | WO-01/27123 | 4/2001 |
|---|---|---|
| WO | WO-02/056889 | 7/2002 |
| WO | WO-02067953 | 9/2002 |
| WO | WO-2007002739 A2 | 1/2007 |

OTHER PUBLICATIONS

Anderson, R., "Chromium Metabolism and its Role in Disease Processes in Man," *Clin. Physiol. Biochem* 4:31-41 (1986).
Cooper et al., "Structure and Biological Activity of Nitrogen and Oxygen Coordinated Nicotinic Acid Complexes of Chromium," *Inorganica Chimica Acta*, 91:1-9 (1984).
Cooper et al., "Chromium (III) Complexes and their Relationship to the Glucose Tolerance Factor Part 2: Structure and Biological Activity of Amino Acid Complexes," *Inorganica Chimica Acta*, 92:23-31 (1984).
Evans et al., "Chromium Picolinate Increases Membrane Fluidity and Rate of Insulin Internalization," Journal of inorganic Biochemistry 46:243-250 (1992).
Gonzalez-Vergara et al., "Chromium Coordination Compounds of Pyridoxal and Nicotinic Acid: Synthesis, Absorption and Metabolism," *Israel Journal of Chemistry*, 21:18-22 (1981).
Grant et al., "Chromium and exercise training: effect on obese women," Med. Sci. Sports Exerc. 29(8): 992-998 (1997).
Kane-McGuire et al., "Synthesis, Characterization, and Photobehavior of Δ- and Δ-fac-Tris((S)-tryptophanato)chromium(III)," *Inorg, Chem.* 34:1121-1124 (1995).
Lukaski, H., "Chromium as a Supplement," *Annu. Rev. Nutr.* 19:279-302 (1999).
Maciejewska et al., "Homo- and hetero-nuclear chromium(III) complexes with natural ligands. Part 1: Spectroscopic and mass spectra studies on ternary [M-L1-L2] systems," *Transition Metal Chemistry* 27:473-480 (2002).
Mertz, W., "Chromium Occurrence and Function in Biological Systems," Physiological Reviews 49(2): 163-239 (Apr. 1969).
Olin et al., "Comparative retention/absorption of 51chromium (51Cr) from 51Cr chloride, 51Cr nicotiniate and 51Cr picolinate in a rat model," *Trace Elements and Electrolytes* 11 (4):182-186 (1994).
Preuss et al., "Comparative Effects of Chromium, Vanadium and *Gymnema sylvestre* on Sugar-Induced Blood Pressure Elevations in SHR," *Journal of the American College of Nutrition* 17(2):116-123 (1998).
Preuss et al., "Chromium update: examining recent literature 1997-1998," *Current Opinion in Clinical Nutrition and Metabolic Care* 1:509-512 (1998).
Preuss et al., "Effects of a natural extract of (-)hydroxycitric acid (HCA-SX) and a combination of HCA-SX plus niacin-bound chromium and *Gymnema sylvestre* extract on weight loss," *Diabetes, Obesity and Metabolism* 6:171-180 (2004).
Preuss et al., "Efficacy of a novel, natural extract of (-)hydroxycitric acid (HCA-SX) and a combination of HCA-SX plus niacin-bound chromium and Gymnema sylvestre extract in weight managenment in human volunteers: A pilot study," Nutritional Research 24:45-58 (2004).
Toepfer et al., "Preparation of Chromium-Containing Material of Glucose Tolerance Factor Activity from Brewer's Yeast Extracts and by Synthesis," J. Agric. Food Chem. 25(1):162-166 (1977).
Vicens et al., "Some new chromium (III) complexes of nicotinic acid; a D NMR and EPR study," Inorganica Chimica Acta 192:139-142 (1992).
Vincent, J., "Quest for the Molecular Mechanism of Chromium Action and Its Relationship to Diabetes," Nutrition Reviews 58(3):67-72 (2000).
Yang et al., "A newly synthetic chromium complex-chromium(phenylalanine)3 improves insulin responsiveness and reduces whole body glucose tolerance," FESB Letters 579:1458-1464 (2005).

\* cited by examiner

TRIVALENT CHROMIUM COMPOUNDS, COMPOSITIONS AND METHODS OF USE

This application is a divisional which claims benefit to continuation application Ser. No. 12/251,310, filed Oct. 14, 2008, which is a continuation-in-part of PCT/US2007/066544, filed Apr. 12, 2007, which claims the benefit of priority from provisional patent application Ser. No. 60/791,286, filed Apr. 12, 2006, all of which are incorporated in their entirety by reference herein.

FIELD OF THE INVENTION

The present invention relates generally to novel trivalent chromium complexes, which possess the ability to improve insulin sensitization, glucose tolerance, blood lipid profiles, and lean body mass through increased chromium bioavailability, efficacy and safety. More specifically, the present invention relates to compositions containing trivalent chromium complexes having two nicotinic acid ligands and a third ligand selected from the group consisting of alanine, aspartic acid, asparagine, arginine, cysteine, glutamic acid, glutamine, histidine, isoleucine, lysine, leucine, methionine, phenylalanine, proline, serine, threonine, tyrosine, tryptophan, valine, gallic acid, cinnamic acid, hydroxycitric acid, and 5-hydroxytryptophan with cysteine being particularly preferred for treatment of various conditions

BACKGROUND OF THE INVENTION

Although the physiological mechanism is not completely understood, it has been reported that animals placed on a purified, chromium-free diet for several weeks displayed greatly impaired glucose tolerance, i.e. the ability to maintain blood glucose at normal levels. It was found that a diet containing chromium-rich Brewer's yeast would eliminate this impairment and that blood glucose levels would return to normal. The presence of chromium as an organic salt in foods was also found to increase glucose oxidation in humans, particularly when extracts of Brewer's yeast containing chromium where added. In addition, oral administration of such material to a diabetic individual was found to influence the pancreas to produce normal amounts of insulin.

The relationship between chromium content in food and its effects on glucose oxidation are discussed, for example in Toepfer, et al., "Chromium Foods in Relation to Biological Activity," J. Agr. Food. Chem. 21:69 (1973).

Trivalent chromium ($Cr^{+3}$) has long been known to be essential for proper insulin function and, thus, plays a vital role in protein, fat and carbohydrate metabolism. In the U.S., studies show that the diets of nine out of 10 Americans are deficient in chromium, while chromium levels are known to decline with age. Stress, exercise and pregnancy are known to increase chromium losses from the body. Chromium deficiency can lead to symptoms associated with adult-onset diabetes, obesity and cardiovascular disease. In studies, supplemental trivalent chromium has improved blood sugar levels or other symptoms in people with glucose intolerance, type 1 diabetes, type 2 diabetes, steroid-induced diabetes and gestational diabetes. Chromium is also known to increase lean body mass, improve blood lipid profiles and lower blood pressure levels. However, chromium bioavailability and biological activity are dependent upon the ligand to which chromium is bound. (Mertz, W. Chromium Occurrence and Function in Biological Systems, Physiological Reviews, 49(2): 163-239, 207, 1969 (and see generally for a discussion of chromium's biological function).

Inorganic chromium chloride, for example, is poorly absorbed by the body, typically less than one percent, and has poor bioavailability. Elucidating the structure, function and mode of action of the biologically active form of chromium, however, has proved enigmatic. (Mertz W. Chromium in human nutrition: a review. J. Nutr. 1993; 123:626-633; Lukaski H. C. Chromium as a supplement. Annu. Rev. Nutr. 1999; 19:279-301.)

Various proposals have been developed as to the composition of a biologically active chromium composition called glucose tolerance factor (GTF). Walter Mertz has suggested that Brewer's yeast contained a biologically active form of trivalent chromium comprised of $Cr^{3+}$, glycine, glutamate, cysteine, and nicotinic acid, which strongly potentiated the action of insulin and possess an ultraviolet absorbance maximum at about 260 nm. (Schwartz K, Mertz W: A glucose tolerance factor and its differentiation from factor 3. *Arch Biochem Biophys* 72: 515-518, 1957; Toepfer E W, Mertz W, Polansky M M, Roginski E E, Wolfe W R: Preparation of chromium containing material of glucose tolerance factor activity from Brewer's yeast extracts and by synthesis. *J. Agricul Food Chem* 25: 162-166, 1977.) However, extracting the biologically active fractions of chromium in Brewer's yeast involves complex processes, which are expensive on a commercial scale for use in chromium supplementation of chromium deficient diets or for individuals otherwise requiring chromium supplementation. Therefore, researchers have tried to overcome this problem by synthetically preparing biologically active chromium compounds. In this regard, see Cooper et al., Inorganica Chimica Acta 92:23-31 (1984), which is directed to the synthesis and analysis of possible components of GTF. In Cooper, various complexes of glycine, glutamic acid, glutamine, cysteine and nicotinic acid were formed and analyzed for glucose tolerance factor activity using a yeast assay. A number of complexes including $Cr$-$(cysteine)_2^-$, Cr-nicotinic acid-cysteine complexes of undetermined structure, and Cr-nicotinic acid glycine were tested but only $Cr(glutamine)_2(H_2O)_2^+$, Cr-nicotinic acid-glycine and the mixture of complexes of $Cr(glycine)_n(H_2O)_{6-n}^{+3}$ showed significant activity. In contrast, $Cr(cysteine)_2^-$ and Cr-nicotinic-cysteine complexes were not active in the yeast bioassay.

Other chromium complexes have been proposed as well. Maciejewska et al., Transition Metal Chem. 27:473-480 (2002) tested the toxicity and determined structure data of seven mono- and poly-nuclear $Cr^{III}$ complexes with natural ligands: glycine, glutaminic, nicotinic and asparginic acid, cysteine, and glutathione. Gonzales-Vergara et al., Israel J. Chem. 21:18-22 (1981) synthesized $CrCl_3$, CrEDTA, $Cr(glycine)_2(nicotinic\ acid)_2$, Cr(III)-pyridoxylideneglycyl-glycine-diaquo (Cr(III)-PGG-diaquo), and Cr(III)-PGG-(nicotinic acid)$_2$, which were tested for retention in mice.

The importance of the B vitamin, niacin, to chromium's biological activity was elucidated by Walter Mertz, when it was discovered that chromium bound to niacin strongly potentiated the action of insulin in vitro, while chromium alone, niacin alone or chromium bound to isomers of niacin, including picolinic acid, had virtually no effect on insulin in vitro. (Mertz W, Effects and Metabolism of Glucose Tolerance Factor, *Present Knowledge in Nutrition*, 4$^{th}$ Edition, The Nutrition Foundation, Washington, D.C., Chapter 36, pp 365-372, 1976.)

Niacin can be bound to chromium in various configurations. A particular oxygen-coordinated niacin-bound chromium complex was developed and introduced commercially as ChromeMate® (Interhealth Nutraceuticals, Inc., Benecia, Calif.). (Jensen, U.S. Pat. No. 5,194,615). Subsequently, Cooper et al. determined that oxygen-coordinated niacin-bound chromium was up to 18-times more potent than other forms of niacin-bound chromium tested in vitro. (Cooper J, et al, Structure and Biological Activity of Nitrogen and Oxygen Coordinated Nicotinic Acid Complexes of Chromium, *Inorganica Chimica Acta,* 91:1-9, 1984.)

Further studies established the superior safety and efficacy of ChromeMate® over inorganic chromium chloride and chromium picolinate, two commercially available forms of trivalent chromium for dietary supplementation. (Jain S K, Rains J and Rogier K, Effect of Niacin-Bound Chromium Complex (NBC) on IL-6 Secretion and Oxidative Stress Caused by High Glucose (HC) in Cultured U397 Monocytes, *FASEB,* 20(4):132, Abs. 376.4, April 2006; Grant K E, Chandler R M, Castle A L, Ivy J L, Chromium and Exercise Training: Effect on Obese Women, *Medicine & Science in Sports & Exercise,* 29:992-998, 1997; Preuss H G, Gropec P L, Lieberman S and Anderson R A, Effects of Different Chromium Compounds on Blood Pressure and Lipid Peroxidation in Spontaneously Hypertensive Rats, *Clinical Nephrology,* 47:325-330, 1997; Stearns D M, Wise, Sr., J P, Patierno S R and Wetterhahn K E, Chromium (III) Picolinate Produces Chromosome Damage in Chinese Hamster Ovary Cells. *The FASEB Journal,* 9: 643-1648, 1995.) In human bioavailability equivalence studies, researchers at U. C. Davis demonstrated that ChromeMate® was 311% more bioavailable than chromium picolinate and 672% more than chromium chloride in animal models. (Olin et al., Comparative retention/absorption of $^{51}$chromium ($^{51}$Cr) from $^{51}$Cr chloride, $^{51}$Cr nicotinate and $^{51}$Cr picolinate in a rat model, *Trace Elements and Electrolytes,* 11(4):182-186, 1994.)

John Vincent has proposed a naturally occurring oligopeptide, low-molecular-weight chromium-binding substance (LMWCr) or chromodulin. Chromodulin has been proposed to activate insulin receptor kinase activity. The oligopeptide possesses a molecular weight of 1500 Da and is comprised of four types of amino acid residues: glycine, cysteine, glutamate and aspartate. (Vincent J. B: The quest for the molecular mechanism of chromium action and its relationship to diabetes. *Nutr. Rev.* 58, 2000.)

Taken together, the ligands of four amino acids, glycine, cysteine, glutamate and aspartate, and niacin are important for bioactive chromium complexes. (Yamamoto A., Wada O, Ono T: Isolation of a biologically active low-molecular-mass chromium compound from rabbit liver. *Eur. J. Biochem.* 165: 627-631, 1987; Davis C M, Vincent J B, Chromium oligopeptide activates insulin receptor tyrosine kinase activity. *Biochemistry* 36: 4382-4385, 1997.)

Another proposal supports the use of the amino acid histidine for GTF activity, U.S. Pat. No. 6,689,383, which is incorporated by reference in its entirety. Chromium histidine is said to be absorbed at least 50 percent better than chromium picolinate. In tests, men and women absorbed an average 3.1 μg of chromium from the chromium-histidine complex, compared with 1.8 μg from chromium picolinate, 0.4 μg from chromium chloride and 0.2 μg from chromium polynicotinate.

Alternatively, Yang et al. have shown the use of triphenylalanine as a ligand for a bioactive form of chromium. (Yang X, Palanichamy K, Ontko A C, Rao M N A, Fang C, Ren J, Sreejayan N: A newly synthetic chromium complex—chromium triphenylalanine improves insulin responsiveness and reduces whole body glucose tolerance, *FEBS Letters* 579 1458-1464, 2005.)

Synthesis of chromium amino acid nicotinate complex with mixture of glycine, glutamic acid and cysteine has been disclosed in U.S. Pat. No. 5,536,838, which is incorporated by reference in its entirety.

Chromium (III) 1:3 complexes of alpha amino acids are disclosed as animal nutritional supplements in Abdel-Monem et al., U.S. Pat. No. 7,247,328. Exemplified amino acids are methionine and leucine.

Gillota, U.S. Patent Publication No. 2003/0143311, discloses a recovery drink formula that includes chromium in the form of chromium dinicotinate glycinate.

In addition to a desire for safety, efficacy and bioavailability, there remains a desire for stability, solubility and the effect on taste and odor for use in food and beverage applications. Thus, while there have been many proposed chromium complexes for use in dietary supplements and food and beverage applications, most are inadequate or poorly characterized, and there still remains a need in the art for an improved synthetic chromium compound, which demonstrates improved biological activity, bioavailability, stability, solubility and/or sensory characteristics.

SUMMARY OF THE INVENTION

The present invention relates to the discovery that chromium dinicocysteinate is characterized by improved physical properties and by increased chromium bioavailability and efficacy once administered to a subject. Chromium dinicocysteinate is a trivalent chromium complex with two nicotinic acid ligands and one cysteine ligand, also known as chromium dinicotinocysteinate, dinicotino cysteinato chromium complex, or chromium dinicotinate cysteinate. In addition to chromium dinicocysteinate, disclosed herein are various other chromium complexes, compositions comprising chromium complexes, and methods of using these complexes to promote or improve various health conditions and functions of the body.

Methods of administering these complexes to treat or prevent conditions including but not limited to diabetes, symptoms associated with diabetes, and/or the onset of diabetes include administering a biologically effective amount of chromium dinicocysteinate. Chromium dinicocysteinate demonstrates reductions in fasting glucose levels, glycated hemoglobin, C-reactive protein, monocyte chemotactic protein-1, intracellular adhesion molecule, and red blood cell lipid peroxidation. In addition, it demonstrated elevation of adiponectin and vitamin C levels, which reduces the risk of developing diabetes. Preferably, the biologically effective amount is about 10 μg to about 1000 μg of elemental chromium, and more preferably, 400 μg of elemental chromium. The methods can further comprise treating the symptoms by lowering the blood levels of one or more of fasting glucose, glycosylated hemoglobin, C-reactive protein, monocyte chemotactic protein-1, intracellular adhesion molecule, and red blood cell lipid peroxidase, or by increasing the blood levels of one or both of vitamin C and adiponectin.

Disclosed herein are methods directed to treating the symptoms associated with cardiovascular disease including administering a biologically effective amount of chromium dinicocysteinate. Cardiovascular disease can be treated by lowering elevated LDL cholesterol, VLDL cholesterol, triglycerides, C-reactive protein, blood pressure, and/or vascular inflammation levels, or by increasing HDL cholesterol levels. For example, the disclosed complexes, particularly chromium dinicocysteinate, demonstrate reduction in C-reactive protein, which correlates to cardiovascular disease.

Disclosed herein are methods directed to treating symptoms associated with obesity and overweight individuals including administering a biologically effective amount of chromium dinicocysteinate. Symptoms associated with obesity and overweight individuals can be treated by lowering body weight, body fat, and/or body mass index, and/or increasing lean body mass. For example, the disclosed complexes, particularly chromium dinicocysteinate, demonstrate a reduction in food intake.

In various embodiments, the subject is a mammal. In specific embodiments, the subject is human or swine. In alternative embodiments, the subject is avian.

In still another aspect, disclosed herein are compositions including the disclosed chromium complexes. The compositions can include a pharmaceutically acceptable carrier or a food safe carrier. In some embodiments, the amount of chromium complex in the composition is about 0.000001% to about 1% by weight of the total composition. In various embodiments, the compositions disclosed herein are formulated as a pill, tablet, capsule, powder, lozenge, gum, liquid, solution, dietary supplement, food, beverage, or topical composition.

Novel chromium compounds, which improve insulin sensitization, glucose metabolism or tolerance, blood lipid metabolism, bioavailability and/or safety as compared to chromium nicotinate, chromium picolinate and chromium histidine are disclosed. These compounds were evaluated in terms of solubility, in vitro insulin sensitization, stability, and absorption as compared to chromium nicotinate, chromium picolinate and chromium histidine. The most promising chromium compounds have been tested for their animal in vivo bioavailability, glucose metabolism, lipid metabolism and acute toxicity.

In another embodiment, disclosed herein are chromium compounds (alternatively called chromium complexes) include dinicotinate chromium complexes having a carboxylate ligand as a third ligand. The third ligand can be selected from the group consisting of alanine, aspartic acid, asparagine, arginine, cysteine, glutamic acid, glutamine, histidine, isoleucine, lysine, leucine, methionine, phenylalanine, proline, serine, threonine, tyrosine, tryptophan, valine, gallic acid, cinnamic acid, hydroxycitric acid, and 5-hydroxytryptophan. These complexes can be administered to treat or prevent diabetes, the symptoms associated with diabetes, and/or the onset of diabetes. These complexes can be administered to treat the symptoms associated with cardiovascular disease. In addition, these complexes can be administered to treat associated with obesity and overweight individuals. The third ligand can be a simple carboxylate (e.g., propionate), a carboxylate having other coordinating functionality (e.g., amino acids or hydroxy-acids), and/or a carboxylate having pi electrons available for potential secondary bonding to chromium through chromium's d-orbitals (e.g., tyrosine or tryptophan).

Additional features of the invention may become apparent to those skilled in the art from a review of the following detailed description, taken in conjunction with the drawings, the examples, and the appended claims.

DETAILED DESCRIPTION OF THE INVENTION

Chromium complexes disclosed herein are complexes of chromium having two nicotinic acid ligands and a third ligand having a carboxylate functional group, such as glutamate, cysteine, aspartate, tryptophan, cinnamate, and the like. Preferred compositions include an amino acid as the third ligand, preferably cysteine. These complexes have been compared in various biologically assays for their ability to increase and/or influence the bioavailability and/or biological activity of chromium.

In an embodiment, disclosed herein are complexes of chromium and one, two, or three ligands selected from the group consisting of glycine, alanine, aspartic acid, asparagines, arginine, cysteine, glutamic acid, glutamine, histidine, isoleucine, lysine, leucine, methionine, phenylalanine, praline, serine, threonine, tyrosine, tryptophan, valine, gallic acid, cinnamic acid, hydroxycitric acid, 5-hydroxytrytophan, and nicotinic acid.

In various cases, the ligand(s) has/have the ability to bond to chromium via its carboxylate functional group as well as through pi electron-d orbital interaction. This secondary interaction between the ligand and chromium can increase the bioavailability and absorption of chromium.

In still another aspect, the chromium complexes are complexes of trivalent chromium and at least one and no more than three tyrosine or tryptophan ligands. In specific embodiments, the present invention provides chromium complexes such as chromium (III) tris(tryptophan) and chromium (III) tris(tyrosine).

In another aspect, the chromium complexes are complexes of trivalent chromium and one or more compounds extracted from plants. The plants from which these compounds are extracted are typically plants shown to have beneficial health benefits, such as genus *Garcinia, Groffonia simplicifolia*, cinnamon bark, gallnuts, sumac, witch hazel, tea leaves, and oak bark. In specific embodiments, the present invention provides chromium complexes such as chromium hydroxycitrate, chromium hydroxytryptophan, chromium cinnamate, and chromium gallate.

In some cases, the ligand has known biological function alone. Examples include, but are not limited to, hydroxycitric acid, 5-hydroxytryptophan, gallate, and cinnamate.

In yet another aspect, methods are disclosed for improving or promoting healthy insulin function, glucose tolerance, blood sugar levels, blood lipid levels, blood pressure levels, inflammation, and/or lean body mass comprising administering a biologically effective amount of a composition as disclosed herein to a subject in need thereof, wherein the composition provides sufficient chromium to the subject and improves or promotes one or more of the identified health conditions, which are now known or are discovered to be responsive to chromium levels in the subject.

Inflammation

It is contemplated that the disclosed compounds are useful for treating symptoms associated with inflammation. Inflammation is the complex biological response of vascular tissues to harmful stimuli, such as pathogens, damaged cells, or irritants. It is a protective attempt by the organism to remove the injurious stimuli as well as initiate the healing process for the tissue.

Chronically inflamed tissue is characterized by the infiltration of mononuclear immune cells, including monocytes, macrophages, lymphocytes, and plasma cells. Nuclear factor kappa B (NF-κB) also plays an important role in inflammation through modulation of proinflammatory cytokines including, for example, interleukin 6 (IL-6), interleukin 17A (IL-17A), and tumor necrosis factor-alpha (TNFα). Increased levels of monocyte chemotactic protein-1 (MCP-1), C-reactive protein (CRP), and oxidative stress and decreased levels of adiponectin are known to increase vascular inflammation. The compounds disclosed herein, specifically chromium dinicocysteinate for example, demonstrate reductions in CRP and MCP-1, and increases in adiponectin, and are contemplated to be useful in the treatment of inflammatory conditions, such as, hay fever, rheumatoid arthritis, and atherosclerosis, which is a chronic inflammatory response in the wall of arteries.

Reduced Oxidative Stress

According to another embodiment, it is contemplated that the disclosed compounds are useful for reducing oxidative stress. Inflammation and oxidative stress are closely linked. Inflammation and oxidative stress are usually observed in degenerative or chronic diseases. The ZDF rat is a model of type 2 diabetes and is associated with elevated levels of both hyperglycemia and pro-inflammatory cytokines. Hyperglycemia causes excessive oxygen radical production leading to increased oxidative stress in diabetes (Evans et al.: The molecular basis for oxidative stress-induced insulin resistance. *Antioxidant Redox Signaling.* 7:1040-1052, 2005). Oxidative stress also influences the expression of multiple genes in vascular cells, including signaling molecules such as protein kinases (PK) and nuclear factor kappa B (NF-κB). Over-expression of these genes may induce the secretion of pro-inflammatory cytokines. Oxidative stress plays a key role in a cascade of events which results in elevated glucose leading to monocyte and endothelial cell activation and finally the enhanced vascular inflammation observed in diabetes (Guha et al.: Molecular mechanisms of tumor necrosis factor a gene expression in monocytic cells via hyperglycemia-induced oxidant stress-dependent and -independent pathways. *Journal of Biological Chemistry.* 275: 17728-17739, 2000). For example, chromium dinicocysteinate reduced elevated blood lipid peroxidation levels in Zucker diabetic fatty (ZDF) rats. Without intending to be bound by theory, it is believed that the underlying molecular mechanism of the observed beneficial effects of chromium dinicocysteinate are likely to be due to the inhibition of oxidative stress-signaling molecules such PKB and NF-κB.

Improved Liver and Kidney Function

In one embodiment, it is contemplated that the disclosed compounds improve liver and/or kidney function. A recent study showed an inverse correlation of insulin sensitivity to elevated alkaline phosphatase activities in the blood of 472 apparently healthy men (Godsland and Johnston: Co-associations between insulin sensitivity and measures of liver function, subclinical inflammation, and hematology. Metabolism *Clinical and Experimental.* 57:1190-7, 2008). The liver plays an important role in maintaining normal glucose concentrations during fasting as well as postprandial. Insulin dysfunction leads to ineffective suppression of hepatic glucose production and glycogenolysis in the liver causing an increase in hepatic glucose production (Michael and Kulkarni: Loss of Insulin signaling in hepatocytes leads to severe insulin resistance and progressive hepatic dysfunction. *Molecular Cell.* 6:87-97, 2000). Evidence also indicated that liver function and subclinical inflammation are related to insulin sensitivity which predict new-onset of type 2 diabetes independent of classical risk factors (Hsiao et al.: Decreased Insulin Secretion and Insulin Sensitivity Are Associated With Liver Function in Subjects With Fasting Glucose Between 100 and 109 mg/dL in Taiwanese Population. *Pancreas* 35:343-7, 2008). Without intending to be bound by theory, it is believed that a decrease in the alkaline phosphatase activities in the chromium dinicocysteinate-supplemented group suggests an improvement in liver function which may play a role in the improved glycemia-related parameters as observed in the chromium dinicocysteinate-supplemented Zucker diabetic fatty rats. For example, chromium dinicocysteinate reduces alkaline phosphatase activities. In addition, chromium dinicocysteinate can improve kidney and/or endothelial cellular functions by reducing blood creatinine.

Compositions of Chromium Complexes

The chromium complexes disclosed herein can be incorporated into a composition. These compositions can further comprise a pharmaceutically acceptable carrier or excipient or a food safe carrier or excipient. The amount of the chromium complex is typically about 0.000001% to about 1% by weight of the total composition. The chromium complex can be about 0.00001% to about 0.5%; about 0.00001% to about 0.1%; about 0.001% to about 0.5%, or about 0.001% to about 0.01% by weight.

The compositions disclosed herein typically provide a total amount of chromium upon administration to a subject in need of about 10 μg to about 1000 μg. The amount of chromium provided can be about 20 μg to about 500 μg; about 20 μg to about 250 μg; about 100 μg to about 750 μg; about 250 μg to about 750 μg; or about 500 μg to about 1000 μg.

An "effective amount" of the disclosed complexes refers to the amount or quantity of the complex, which is sufficient to elicit the required or desired prophylactic or therapeutic response, or in other words, the amount which is sufficient to elicit an appreciable biological response when administered to a subject. For example, an effective amount of a chromium complex as disclosed herein may reduce blood sugar levels in a subject. The actual effective amount for a particular subject can be readily determined by a person of ordinary skill in the art by various dosing tests and evaluations of chromium complexes for their effect on, for instance, fasting glucose levels, blood vitamin C levels, and the like. For example, in the study disclosed in the Example section below, a biologically effective amount for obese Zucker rats was 400 μg per kilogram body weight.

The compositions disclosed herein comprise a pharmaceutically acceptable carrier or a food safe carrier. Such carriers can be those that are approved by regulatory agencies, such as the U.S. Food and Drug Administration and its national counterparts or those carriers generally regarded as safe (GRAS) in the relevant industry. Exemplary carriers include phosphate buffered saline solution, and 5% aqueous solution of dextrose. The present compositions can be in the form of an emulsion, such as an oil/water or water/oil emulsion, and various types of wetting agents and/or adjuvants, that are approvable by a competent regulatory authority as suitable for administration. Suitable pharmaceutical carriers and formulations are described in Remington's Pharmaceutical Sciences, 19th Ed. (Mack Publishing Co., Easton, 1995).

Preferred pharmaceutical carriers depend upon the intended mode of administration of the active agent. Typical modes of administration include enteral (e.g., oral), topical, or parenteral (e.g., subcutaneous, intramuscular, intravenous, intraperitoneal or intrathecal injection; transdermal, or transmucosal, including intrapulmonary administration). Pharmaceutically acceptable ingredients are well known for the various types of compositions and may be, for example, binders such as natural or synthetic polymers, excipients, lubricants, surfactants, sweetening and flavoring agents, coating materials, preservatives, dyes, thickeners, adjuvants, antimicrobial agents, antioxidants and carriers for the various formulation types. Nonlimiting examples of binders useful in a composition described herein include gum tragacanth, acacia, starch, gelatin, and biological degradable polymers such as homo- or co-polyesters of dicarboxylic acids, alkylene glycols, polyalkylene glycols and/or aliphatic hydroxyl carboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol and esters or -ethers thereof, poly-vinylimidazole, poly-vinylpyrrolidon, and natural polymers like chitosan.

Nonlimiting examples of excipients useful in a composition described herein include phosphates such as dicalcium phosphate. Nonlimiting examples of lubricants use in a composition described herein include natural or synthetic oils, fats, waxes, or fatty acid salts such as magnesium stearate.

Surfactants for use in a composition described herein can be anionic, cationic, amphoteric or neutral. Nonlimiting examples of surfactants useful in a composition described herein include lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Nonlimiting examples of sweetening agents useful in a composition described herein include sucrose, fructose, lactose, aspartame, saccharine, acesulfame potassium, or sucralose. Nonlimiting examples of flavoring agents for use in a composition described herein include peppermint, oil of wintergreen or fruit flavors such as cherry or orange flavor. Nonlimiting examples of coating materials for use in a composition described herein include gelatin, wax, shellac, sugar or other biological degradable polymers. Nonlimiting examples of preservatives for use in a composition described herein include methyl or propylparabens, sorbic acid, chlorobutanol, phenol and thimerosal.

Additionally or alternatively, the present chromium compositions can be incorporated into food or beverages. Juices, energy drinks, diet drinks, protein bars, and the like can be used as a vehicle for oral delivery of the present chromium compositions.

Screening of Novel Chromium Complexes

Three phases of screening of chromium compounds were conducted. Phase I included synthesis and chemical/physical characterization of the novel chromium complexes in comparison to know (reference or control) compounds. Phased II included in vitro insulin sensitization, absorption and stability tests on all of the synthesized chromium complexes as compared to reference or control compounds, such as chromium nicotinate, chromium picolinate, chromium histidine and chromium triphenylalanine. Phase III included in vivo bioavailability, glucose metabolism, lipid metabolism and acute toxicity.

Still another set of chromium complexes disclosed herein are chromium having three different carboxylate ligands. By varying ligands from nicotinic acid, glutamate, cysteinate, aspartate, arginiate, tyrosine and tryptophan, at least 30 possible chromium complexes are produced. Each of these compounds can be assessed for their ability to provide chromium in a bioavailable form using the assays disclosed herein.

Some chromium compounds contemplated include, but are not limited to, the following: Chromium dinicocysteinate; Chromium dinicotinate tryptophan; Chromium dinicotinate tyrosine; Chromium dinicotinate hydroxycitrate; Chromium dinicotinate cinnamate; Chromium dinicotinate gallate; Chromium dinicotinate 5-hydroxytryptophan; Chromium dinicotinate aspartate; Chromium dinicotinate glutamate; Chromium dinicotinate arginate; Chromium tris(tryptophan); Chromium tris(tyrosine); Chromium tris (hydroxycitrate); Chromium tris(5-hydroxytryptophan); Chromium tris(cinnamate); and Chromium tris(gallate).

Chromium Hydroxycitrate

Hydroxycitric acid (HCA) is a naturally occurring acid found in the rinds of the fruit of *Garcinia cambogia, Garcinia indica, Garcinia mangostana*, and *Garcinia atrovirides*. The dried fruit rind of *G. cambogia*, also known as Malabar tamarind, is commonly used in Southeast Asia (particularly southern India) as a food preservative, flavoring agent and carminative. The primary mechanism of action of (−)-HCA appears to be related to act as a competitive inhibitor of the enzyme ATP-citrate lyase, which catalyzes the conversion of citrate and coenzyme A to oxaloacetate and acetyl coenzyme A (acetyl-CoA), building blocks of fatty acid synthesis. Extensive experimental studies suggest that (−)-HCA suppresses fatty acid synthesis, lipogenesis and food intake, thus leading to weight reduction. In addition to suppression of fatty acid and fat synthesis, (−)-HCA is thought to suppress food intake via loss of appetite by stimulation of liver gluconeogenesis. Various researchers have evaluated HCA for its weight control properties, fat burning properties, lipid level lowering effect, appetite regulation, metabolic rate increase and other effects. A number of patents have been granted based on the above studies and various methods of extraction of HCA from the fruit. The isolation and chemical nature of (−)-HCA from *Garcinia* rind are well studied. (See, e.g., Lewis, Y. S. et al, *Phytochemistry*, 4, 619-625, 1965; U.S. Pat. No. 5,656,314, which is incorporated by reference in its entirety.) Recent literature reveals that (−)-HCA acts as a glucose absorption regulator. (See, e.g., Wielinga, Y. P. et al. Hydroxycitric acid delays glucose absorption in rats, *Am. J. Physiol. Gastrointest. Liver Physiol.*, 288:1144-1149, 2005). Since HCA alone has been shown to have beneficial effects in regulating glucose absorption and in weight control, HCA complexed to chromium provides a doubly beneficial effect—through the effect of HCA and through the effect of bioavailable chromium.

Chromium Cinnamate or Chromium Gallate

Cinnamic acids are widely distributed in plant kingdom and are reported as antioxidants. These compounds impart nutraceutical traits to foods by way of their abilities to serve as cellular antioxidants, anti-inflammatory agents or inhibitors of enzymes involved in cell proliferation. These activities are important in ameliorating chronic diseases such as cancer, arthritis and cardiovascular disease, which in some cases may be caused by free radicals. Because of proven safety of cinnamic acids like caffeic acid and phenolic benzoic acids like gallic acid, chromium complexes of cinnamic acid and gallic acid may have insulin sensitizing capacity.

Chromium 5-Hydroxytryptophan Complex

5-Hydroxytryptophan (5-HTP) is a natural compound isolated from the seeds of an African plant called *Griffonia simplicifolia*. Substances which increase brain serotonin (5-hydroxytryptamine, 5-HT) are effective anorectic agents to help obese patients lose weight and to decrease cravings for sweets and carbohydrates. Experimental studies have proven that 5-HTP increases brain serotonin (5-HT), a neurotransmitter involved in appetite control, sleep and mood. Chromium complexes of 5-hydroxytryptophan may exhibit these same beneficial effects in addition to the beneficial effects due to bioavailable chromium.

Synthesis and Characterization of Chromium Complexes and Reference Compounds Synthesis and characterization of chromium complexes disclosed herein is performed according to the methods disclosed in the examples below.

Chromium compounds were screened employing the following in vitro assays as compared to known chromium complexes: chromium nicotinate, chromium picolinate, chromium histidine, chromium triphenylalaine and chromium nicotinoglycinate: 1. Solubility analysis; 2. Insulin sensitivity and glucose metabolism/utilization assay; 3. Stability analysis (time, temperature and pH); 4. Cytotoxicity assay (lactate dehydrogenese leakage assessment); 5. Absorption study using the intestinal reperfusion model.

The most promising compounds were tested employing the following assays as compared to other chromium complexes: chromium nicotinate, chromium picolinate, chromium histidine, chromium triphenylalaine and chromium nicotinoglycinate: 1. Bioavailability; 2. Glucose metabolism/uptake/utilization; 3. Insulin sensitivity; 4. Lipid metabolism (animal in vivo); 5. Acute toxicity ($LD_{50}$).

EXAMPLES

Tryptophan-Chromium Complex

Method I
The synthesis was made effective through an intermediate of tris-(ethylenediamine) chromium.

Synthesis of tris(ethylenediamine)chromium

Zinc metal (1 g) was added to a solution of chromium(III) chloride ($CrCl_3.6H_2O$, 26.6 g, 0.11 mole) in methanol (50 mL). The mixture was refluxed at 70-80° C. Anhydrous ethylenediamine (36 g, 0.6 mole) was added drop-wise to the refluxing chromium salt solution and the refluxing was continued for one hour. The solution was cooled, filtered and the yellow product, washed first with 10% ethylenediamine solution in methanol (75 mL) and then with ether. Finally the product was dried in air (yield 19 g).

Synthesis of Tris(Tryptohanato)Chromium

Tris(ethylenediamine)chromium (0.6 g, 1.9 mmol) was added to a stirred suspension of hot L-tryptophan (2.0 g, 9.6 mmol) in water (30 mL). The mixture was heated at 80-90° C. refluxed further for 5 hour and the solid product obtained was filtered while hot. The solid was washed with hot water (200 mL) to remove the unreacted starting materials. The product was vacuum dried (0.8 g, 64%). The Electrospray Ionization Mass Spectrum of the compound indicated the peak corresponding to the product.

Method II
A suspension of tryptophan (4.59 g, 22.5 mmol) in water (120 mL) was heated to 70-80° C. A solution of chromium chloride ($CrCl_3.6H_2O$, 1.995 g, 7.5 mmol) in water (15 mL) was added to it and was maintained at this temperature under stirring for 7 h. The resulting mixture was cooled to room temperature, frozen at −80° C. and lyophilized. After lyophilizing for 48 h, the dark purple solid was washed with acetone and air dried to obtain the pure product. The product was subjected to elemental analysis: Calculated for $Cr(TRP)_3.3HCl.2H_2O$: C, 49.11; H, 5.00; N, 10.41; Observed: C, 49.84; H, 5.18; N, 10.41. Electro Spray Ionization Mass Spectrometry: Calculated for $Cr(TRP)_3$: 661; Observed a peak at 662.3 (M+1)

Tyrosine-Chromium Complex

Method I
Due to poor solubility of Tyrosine, even in DMSO, the method I using Cr(en)3 complex did not work well, therefore the second method was adopted for the synthesis.

Method II
A suspension of tyrosine (8.145 g, 44.95 mmol) in water (350 mL) was heated to reflux. A solution of Chromium chloride ($CrCl_3.6H_2O$, 2.66 g, 10 mmol) in DI water (35 mL) was added to it and was maintained refluxing overnight, under stirring. Cooled to room temperature, and filtered the purplish solution (containing lot of un-dissolved white material). The solution was frozen at −80° C. and lyophilized. After lyophilizing for 48 h, the dark purple solid was washed with acetone and finally dried in air to get the pure product. Elemental analysis: Calculated for $Cr(TYR)_3.3HCl.7H_2O$: C, 39.16; H, 5.72; N, 5.07; Observed: C, 39.59; H, 5.12; N, 4.33. Electro Spray Ionization Mass: Calculated for $Cr(TYR)_3$ 592; Observed a peak at 593 (M+1).

5-Hydroxytryptophan Chromium Complex

A suspension of 5-Hydroxytryptophan (2.20 g, 10 mmol) in DI water (100 mL) was heated to 70-80° C. A solution of Chromium chloride ($CrCl_3.6H_2O$, 0.88 g, 3.31 mmol) in DI water (20 mL) was added to it and was maintained at this temperature under stirring for 9 h. Cooled to room temperature, frozen at −80° C. and lyophilized. After lyophilizing for 48 h, the dark purple solid was washed with acetone and finally dried in air to get the pure product. Elemental analysis: Calculated for $Cr(HTRP)_3.3HCl.2H_2O$: C, 46.35; H, 4.72; N, 9.83; Observed: C, 46.17; H, 4.84; N, 9.53. Electro Spray Ionization Mass: Calculated for $Cr(TYR)_3$ 709; Observed a peak at 710 (M+1).

Dinicotino Glutamino Chromium Complex

A suspension of nicotinic acid (3.60 g, 29.24 mmol) in DI water (120 mL) was heated to 70-80° C. Glutamic acid (2.22 g, 15.1 mmol) was added to it and continued heating. Once the whole material was dissolved a solution of Chromium chloride (CrCl$_3$.6H$_2$O, 4.05 g, 15.2 mmol) in DI water (20 mL) was added to it. The mixture was stirred at 70-80° C. for 9 h and cooled to room temperature, frozen at −80° C. and lyophilized. The dark solid obtained was collected and washed with acetone and dried to get the product. Elemental analysis: Calculated for Cr(NIC)$_2$(GLU).3HCl.3H$_2$O: C, 33.73; H, 4.16; N, 6.94; Observed: C, 33.40; H, 3.70; N, 6.91.

Dinicotino Aspartato Chromium Complex

A suspension of nicotinic acid (3.60 g, 29.24 mmol) in DI water (120 mL) was heated to 70-80° C. Aspartic acid (1.99 g, 15.1 mmol) was added to it and continued heating. Once the whole material was dissolved a solution of Chromium chloride (CrCl$_3$.6H$_2$O, 4.05 g, 15.2 mmol) in DI water (20 mL) was added to it. The mixture was stirred at 70-80° C. for 9 h and cooled to room temperature, frozen at −80° C. and lyophilized. The dark solid obtained was collected and washed with acetone and dried to get the product.

Chromium Dinicocysteinate Complex

Nicotinic acid (3.604 g, 29.25 mmol) was dissolved in 100 mL of deionized (DI) water by heating to 80-85° C. Cysteine HCl.H$_2$O (2.65 g, 15.0 mmol) was added as a solid, followed by a 10 mL addition of DI water. The solution was stirred for 5 min, until all the solid had dissolved. CrCl$_3$.6H$_2$O (4.06 g, 15.3 mmol) was slowly added as a solid, followed by a 10 mL rinse of DI water. The solution immediately turned a dark blue-green. The solution was stirred at 75-80° C. for 8 hours. The heat was removed and the reaction was stirred overnight. The cooled solution was frozen and lyophilized to afford 9.2 g of a dark green solid.

Evaluation of Chromium (III) Complexes as Disclosed Herein

Chromium complexes were evaluated for bioavailability and in vivo activity. The compounds were tested in comparison with chromium compounds that are known in the art, including, for example, chromium picolinate and chromium nicotinate.

In Vivo Assessment: Obese Zucker rats were used as an ideal type II diabetic animal model for this evaluation. The rats, obtained at five weeks of age and acclimated for two days, were fasted overnight. The rats were then weighed and had blood collected to obtain a baseline reading. The rats were divided into groups to test each compound and fed a Purina® 5008 lab chow diet (Wilmington, Mass.) for eight weeks.

The compounds tested are listed in Table I below. Chromium-containing compounds were administered daily at 400 μg elemental chromium (III) per kilogram body weight for eight weeks. Niacin, arginine, and cysteine were tested at the amounts equivalent to the individual compound present in the complexes containing 400 μg elemental chromium (III) and niacin, arginine, and cysteine, respectively. Niacin was administered daily at approximately 1.9 mg per kilogram body weight. Arginine and cysteine were each administered daily at approximately 1 mg per kilogram body weight. The control group received saline solution alone daily.

The study monitored the following parameters: (1) body weight; (2) food intake; (3) vitamin C levels; (4) fasting glucose levels; (5) lipid profile (total cholesterol (TC), high density lipoprotein (HDL), and triglycerides (TG)); (6) glycosylated hemoglobin (HbAlc); (7) red blood cell lipid peroxidase (RBC lipid peroxidase); (8) adiponectin; (9) plasma C-reactive protein (CRP); (10) monocyte chemotactic protein (MCP-1); (11) intracellular adhesion molecule (ICAM); (12) glutathione (GSH); (13) retinol binding protein (RBP-4); (14) leptin; (15) cyclic adenosine monophosphate (cAMP); (16) tumor necrosis factor (TNFα); (17) interleukin 6 (IL-6); and (18) oxidative DNA damage (OxyDNA).

Food intake was measured at 5 and 7 weeks. At the end of eight weeks, the rates were fasted overnight and then euthanized. Blood was collected, and the plasma was isolated by centrifugation. CRP, MCP-1, ICAM, and adiponectin levels in the plasma were determined by sandwich ELISA method using commercially available kits from Fisher Thermo Scientific Co. (Rockford, Ill.). Oxidative stress was determined by measuring malondialdehyde (an end product of lipid peroxidation) by its reaction with thiobarbituric acid. Vitamin C concentration in the plasma was also determined.

Glycosylated hemoglobin was determined using Glyco-Tek Affinity column kits and reagents available commercially from Helena Laboratories (Beaumont, Tex.). Glucose levels were determined using glucose oxidase measured with an Accu-Chek® Advantage glucometer available commercially from Boehringer Manheim Corp. (Indianapolis, Ind.).

The following data in Tables II-V demonstrates the beneficial effects of chromium dinicocysteinate, for example, by reducing fasting glucose, glycosylated hemoglobin, C-reactive protein, monocyte chemotactic protein-1, intracellular adhesion molecule, and red blood cell lipid peroxidation. Blood vitamin C levels and adiponectin levels were increased with the administration of chromium dinicocysteinate.

In addition, chromium dinicocysteinate outperformed other chromium compounds known for chromium supplementation, such as, for example, chromium nicotinate and chromium picolinate. Specifically, over chromium nicotinate, chromium picolinate, and chromium histidinate, chromium dinicocysteinate demonstrated decreased levels of fasting glucose, ICAM, C-reactive protein, and glycosylated hemoglobin and increased levels of vitamin C and adiponectin. It also demonstrated lower levels of MCP-1 and red blood cell lipid peroxidase over chromium picolinate. Chromium dinicocysteinate lowered levels of TNFα over chromium picolinate and chromium histidinate. Finally, chromium dinicocysteinate demonstrated reduced food intake, decreased levels of fasting glucose, glycosylated hemoglobin, red blood cell lipid peroxidation, TNFα, OxyDNA, AST and ALT, and increased levels of vitamin C and adiponectin as compared to the chromium nicotinate-glycine-cysteine-glutamic acid GTF complex proposed by Toepfer et al.

The following legend describes each abbreviation used in the following tables for each compound.

TABLE I

Abbreviations of the compounds tested

| Abbreviation | Identification |
| --- | --- |
| BL | Baseline |
| Control | Control |
| CrN | Chromium Nicotinate |

TABLE I-continued

Abbreviations of the compounds tested

| Abbreviation | Identification |
|---|---|
| CrP | Chromium Picolinate |
| CrP + Biotin | Chromium Picolinate + Biotin |
| Cr(nic)$_2$Trp | Chromium Dinicotinate Tryptophanate |
| Cr(nic)$_2$Phe | Chromium Dinicotinate Phenylalanine |
| Cr(nic)$_2$Asp | Chromium Dinicotinate Aspartate |
| Cr(nic)$_2$Glu | Chromium Dinicotiante Glutamate |
| Cr(nic)$_2$Cys | Chromium Dinicocysteinate |
| Cr(nic)$_2$Gly | Chromium Dinicotinate Glycinate |
| Niacin | Niacin |
| Cr(nic)$_2$Arg | Chromium Dinicotinate Argininate |
| Arg | Arginine |
| Cys | Cysteine |
| CrNicGlyCysGlu | Compound according to Toepfer et al.[1] including chromium, nicotinic acid, glycine, cysteine, and glutamic acid |
| CrHis | Chromium Histidinate |
| CrP | Chromium Propanate |
| Cr454 | Chromium 454 ™ is created by the reaction of trivalent chromium with high-activity, water soluble small molecules from a GRAS Brewer's yeast extract |
| CrTrp | Chromium Tryptophanate |
| CrCin | Chromium Cinnamate |
| Cr(5HTP)$_3$ | Chromium tris(5-hydroxytryptophan) |
| Cr(nic)$_2$Gluc | Chromium Glucodinicotinate |
| Cr(Phe)$_3$ | Chromium Triphenylalanine |

[1]Toepfer et al., Preparation of Chromium-Containing Material of Glucose Tolerance Factor Activity from Brewer's Yeast Extracts and by Synthesis, J. Agric. Food Chem., 25(1): 162-166 (1977).

TABLE II

Effect on Blood Lipid Profiles

| | N | Body Weight at Sacrificing (g) | Food Intake 5 wks (g/day) | Food Intake 7 wks (g/day) | Total Cholesterol (mg/dL) | Triglyceride (mg/dL) | HDL (mg/dL) | Total Chol/HDL (ratio) |
|---|---|---|---|---|---|---|---|---|
| Baseline | 27 | 151.72 ± 5.21 | — | — | 128.91 ± 3.25 | 181.26 ± 15.97 | 47.89 ± 1.30 | 2.78 ± 0.05 |
| Control | 25 | 358.73 ± 4.98 | 38.55 ± 1.25 | 37.78 ± 1.33 | 189.31 ± 4.13 | 518.50 ± 24.96 | 69.58 ± 1.43 | 2.84 ± 0.05 |
| CrN | 20 | 366.33 ± 5.88 | 36.52 ± 1.22 | 39.6 ± 1.46 | 184.27 ± 3.94 | 514.49 ± 29.51 | 67.54 ± 1.47 | 2.83 ± 0.05 |
| CrP | 19 | 368.67 ± 5.99 | 35.85 ± 1.05 | 40.79 ± 1.61 | 191.80 ± 6.68 | 625.35 ± 82.99 | 66.01 ± 1.80 | 3.02 ± 0.09 |
| Crp + Biotin | 7 | 364.57 ± 9.65 | 38.00 ± 2.09 | 40.53 ± 1.76 | 187.86 ± 3.65 | 478.71 ± 57.55 | 67.14 ± 1.47 | 2.80 ± 0.07 |
| Cr(nic)$_2$Trp | 7 | 368.57 ± 11.54 | 40.49 ± 1.97 | 40.78 ± 1.29 | 183.17 ± 9.51 | 470.67 ± 71.53 | 69.43 ± 3.20 | 2.86 ± 0.15 |
| Cr(nic)$_2$Phe | 7 | 358.00 ± 5.52 | 38.16 ± 1.17 | 39.22 ± 1.51 | 201.71 ± 7.74 | 583.00 ± 60.36 | 70.43 ± 2.62 | 2.87 ± 0.08 |
| Cr(nic)$_2$Asp | 6 | 375.67 ± 7.38 | 38.90 ± 1.58 | 40.00 ± 0.53 | 202.17 ± 4.21 | 699.67 ± 75.01 | 70.17 ± 1.08 | 2.88 ± 0.07 |
| Cr(nic)$_2$Glu | 7 | 392.86 ± 15.58 | 37.51 ± 2.04 | 39.92 ± 2.17 | 192.14 ± 9.90 | 666.50 ± 89.36 | 65.57 ± 3.22 | 2.94 ± 0.09 |
| Cr(nic)$_2$Cys | 13 | 375.08 ± 7.83 | 34.43 ± 1.10 | 38.62 ± 1.62 | 188.46 ± 5.00 | 550.89 ± 47.96 | 66.46 ± 1.42 | 3.00 ± 0.08 |
| Cr(nic)$_2$Gly | 7 | 371.43 ± 9.54 | 34.29 ± 1.77 | 37.14 ± 1.54 | 193.14 ± 9.84 | 610.33 ± 75.44 | 64.57 ± 2.58 | 3.00 ± 0.13 |
| Niacin | 7 | 368.33 ± 9.90 | 37.92 ± 1.60 | 39.67 ± 2.96 | 192.17 ± 8.97 | 486.67 ± 41.09 | 70.33 ± 2.44 | 2.73 ± 0.06 |
| Cr(nic)$_2$Arg | 6 | 367.33 ± 7.07 | 40.22 ± 1.85 | 45.28 ± 3.15 | 186.16 ± 2.94 | 554.65 ± 26.27 | 69.78 ± 1.84 | 3.00 ± 0.04 |
| Arg | 6 | 378.00 ± 12.07 | 37.73 ± 1.01 | 46.80 ± 3.35 | 173.96 ± 7.99 | 485.74 ± 24.07 | 68.69 ± 3.69 | 2.86 ± 0.11 |
| Cys | 6 | 364.80 ± 13.98 | 39.40 ± 2.24 | 39.87 ± 1.23 | 183.58 ± 8.940 | 503.57 ± 40.47 | 68.26 ± 3.31 | 3.02 ± 0.07 |
| CrNicGlyCysGlu | 6 | 357.33 ± 4.31 | 41.61 ± 2.93 | 42.78 ± 1.97 | 168.08 ± 7.29 | 431.27 ± 40.95 | 69.08 ± 2.72 | 2.73 ± 0.04 |
| CrHis | 6 | 367.00 ± 9.15 | — | — | 189.62 ± 7.86 | 503.93 ± 46.27 | 66.90 ± 2.56 | 2.86 ± 0.05 |
| CrProp | 6 | 338.40 ± 9.39 | — | — | 170.56 ± 6.82 | 456.14 ± 52.20 | 64.19 ± 1.61 | 2.68 ± 0.05 |
| Cr454 | 6 | 352.00 ± 6.02 | — | — | 168.08 ± 10.86 | 507.57 ± 26.83 | 60.95 ± 3.14 | 2.78 ± 0.05 |
| CrTrp | 6 | 417.71 ± 10.95 | — | — | 208.09 ± 13.52 | 921.22 ± 147.69 | 60.54 ± 1.51 | 3.46 ± 0.18 |
| CrCin | 7 | 374.00 ± 5.89 | — | — | 191.11 ± 8.68 | 507.35 ± 47.57 | 65.44 ± 2.10 | 2.94 ± 0.0548 |
| Cr(5HTP)$_3$ | 7 | 343.43 ± 10.10 | — | — | 184.77 ± 5.32 | 452.96 ± 51.83 | 68.84 ± 2.19 | 2.72 ± 0.07 |

TABLE II-continued

Effect on Blood Lipid Profiles

|  | N | Body Weight at Sacrificing (g) | Food Intake 5 wks (g/day) | Food Intake 7 wks (g/day) | Total Cholesterol (mg/dL) | Triglyceride (mg/dL) | HDL (mg/dL) | Total Chol/HDL (ratio) |
|---|---|---|---|---|---|---|---|---|
| Cr(nic)$_2$Gluc | 7 | 387.67 ± 12.06 | — | — | 197.33 ± 6.96 | 534.43 ± 46.77 | 65.71 ± 3.55 | 3.06 ± 0.12 |
| Cr(Phe)$_3$ | 7 | 382.57 ± 17.18 | — | — | 169.68 ± 9.58 | 467.04 ± 43.70 | 60.82 ± 3.91 | 2.84 ± 0.12 |

Each value represents mean ± SE

TABLE III

Effect on Key Biological Parameters

|  | N | Fasting Glucose (mg/dL) | HbA1c (%) | Vitamin C (mg %) | GSH (umol/g) | RBC Lipid Peroxidase (nmol/mL) |
|---|---|---|---|---|---|---|
| Baseline | 27 | 233.74 ± 8374 | 5.61 ± 0.12 | 0.27 ± 0.01 | 4.21 ± 0.11 | 1.35 ± 0.28 |
| Control | 25 | 606.25 ± 21.27 | 16.59 ± 0.19 | 0.15 ± 0.01 | 4.85 ± 0.12 | 2.26 ± 0.08 |
| CrN | 20 | 577.29 ± 21.44 | 15.80 ± 0.24 | 0.16 ± 0.01 | 4.76 ± 0.17 | 1.94 ± 0.12 |
| CrP | 19 | 527.28 ± 23.95 | 15.54 ± 0.30 | 0.15 ± 0.01 | 4.84 ± 0.10 | 2.05 ± 0.12 |
| CrP + Biotin | 7 | 527.14 ± 15.08 | 15.79 ± 0.44 | 0.12 ± 0.01 | 5.25 ± 0.14 | 2.19 ± 0.20 |
| Cr(nic)$_2$Trp | 7 | 513.43 ± 24.15 | 15.55 ± 0.30 | 0.13 ± 0.01 | 5.35 ± 0.14 | 1.96 ± 0.24 |
| Cr(nic)$_2$Phe | 7 | 510.43 ± 25.45 | 15.95 ± 0.24 | 0.15 ± 0.01 | 5.05 ± 0.17 | 1.97 ± 0.14 |
| Cr(nic)$_2$Asp | 6 | 496.33 ± 29.35 | 15.62 ± 0.35 | 0.12 ± 0.01 | 5.15 ± 0.15 | 2.02 ± 0.22 |
| Cr(nic)$_2$Glu | 7 | 490.43 ± 40.69 | 14.69 ± 0.57 | 0.14 ± 0.01 | 5.05 ± 0.26 | 2.30 ± 0.21 |
| Cr(nic)$_2$Cys | 13 | 446.24 ± 31.04 | 14.76 ± 0.51 | 0.18 ± 0.01 | 4.74 ± 0.17 | 1.81 ± 0.12 |
| Cr(nic)$_2$Gly | 7 | 448.29 ± 37.83 | 14.45 ± 0.67 | 0.15 ± 0.01 | 4.86 ± 0.19 | 2.11 ± 0.19 |
| Niacin | 7 | 543.00 ± 20.99 | 15.60 ± 0.47 | 0.15 ± 0.01 | 5.32 ± 0.16 | 1.82 ± 0.16 |
| Cr(nic)$_2$Arg | 6 | 628.87 ± 41.70 | 16.56 ± 0.22 | 0.14 ± 0.01 | 4.89 ± 0.30 | 2.47 ± 0.11 |
| Arg | 6 | 446.60 ± 35.43 | 15.88 ± 0.43 | 0.14 ± 0.01 | 4.77 ± 0.15 | 2.23 ± 0.04 |
| Cys | 6 | 483.49 ± 38.22 | 15.17 ± 0.21 | 0.13 ± 0.01 | 4.70 ± 0.26 | 2.34 ± 0.18 |
| CrNicGlyCysGlu | 6 | 533.63 ± 54.48 | 15.90 ± 0.32 | 0.14 ± 0.01 | 4.72 ± 0.15 | 2.34 ± 0.05 |
| CrHis | 6 | 592.01 ± 34.43 | 15.89 ± 0.37 | — | 4.68 ± 0.28 | 1.91 ± 0.07 |
| CrProp | 6 | 549.49 ± 49.44 | 16.90 ± 0.16 | — | 4.76 ± 0.20 | 2.18 ± 0.28 |
| Cr454 | 6 | 573.60 ± 24.04 | 16.47 ± 0.55 | — | 4.44 ± 0.46 | 2.39 ± 0.45 |
| CrTrp | 7 | 402.77 ± 28.41 | 14.16 ± 0.28 | — | 4.54 ± 0.24 | 1.78 ± 0.12 |
| CrCin | 7 | 557.37 ± 36.91 | 15.61 ± 0.33 | — | 5.00 ± 0.12 | 3.12 ± 0.44 |
| Cr(5HTP)$_3$ | 7 | 585.25 ± 31.23 | 16.15 ± 0.30 | — | 5.04 ± 0.08 | 1.93 ± 0.08 |
| Cr(nic)$_2$Gluc | 7 | 474.38 ± 60.73 | 15.21 ± 0.59 | — | 4.62 ± 0.17 | 2.00 ± 0.12 |
| Cr(Phe)$_3$ | 7 | 549.70 ± 45.16 | 15.04 ± 0.65 | — | 4.50 ± 0.35 | 2.01 ± 0.01 |

Each value represents the mean ± SE.

TABLE IV

Effect on Vascular Inflammation Markers

|  | N | MCP-1 (pg/mL) | CRP (ng/mL) | RBP-4 (ng/mL) | Leptin (pg/mL) | ICAM (pg/mL) | Adiponectin (ng/mL) |
|---|---|---|---|---|---|---|---|
| Baseline | 27 | 2141.63 ± 148.03 | 445.91 ± 10.65 | 46064.49 ± 2301.82 | 329.56 ± 13.92 | 14804.29 ± 466.52 | 38183.23 ± 1392.69 |
| Control | 25 | 4080.10 ± 367.64 | 712.99 ± 20.46 | 49618.54 ± 1914.00 | 412.78 ± 22.70 | 18212.60 ± 530.12 | 11399.80 ± 288.08 |
| CrN | 20 | 3175.02 ± 458.52 | 689.86 ± 17.56 | 48498.10 ± 1656.82 | 374.99 ± 23.90 | 18029.45 ± 333.83 | 10575.95 ± 355.40 |
| CrP | 19 | 4549.99 ± 541.23 | 654.78 ± 27.22 | 49236.91 ± 42144.02 | 399.55 ± 22.51 | 20428.47 ± 1568.35 | 11229.84 ± 564.20 |
| CrP + Biotin | 7 | 2597.63 ± 630.54 | 636.65 ± 27.73 | 53184.29 ± 2391.91 | 284.17 ± 13.21 | 17555.81 ± 484.45 | 8898.57 ± 605.35 |
| Cr(nic)$_2$Trp | 7 | 2607.07 ± 635.54 | 617.66 ± 19.13 | 60017.14 ± 2158.23 | 363.21 ± 17.57 | 17950.97 ± 673.35 | 11752.86 ± 1114.20 |
| Cr(nic)$_2$Phe | 7 | 1755.25 ± 348.03 | 633.55 ± 24.11 | 53891.43 ± 3138.66 | 351.16 ± 11.94 | 17480.50 ± 692.46 | 12712.86 ± 506.92 |
| Cr(nic)$_2$Asp | 6 | 1431.68 ± 351.70 | 602.51 ± 35.00 | 57870.00 ± 7839.39 | 406.15 ± 37.40 | 17985.91 ± 678.21 | 12078.33 ± 755.93 |
| Cr(nic)$_2$Glu | 7 | 3197.58 ± 684.32 | 519.94 ± 21.48 | 46720.00 ± 2053.76 | 378.02 ± 20.80 | 16980.59 ± 375.03 | 12446.67 ± 1420.72 |
| Cr(nic)$_2$Cys | 13 | 2829.17 ± 505.01 | 569.96 ± 24.87 | 49670.13 ± 2905.84 | 407.32 ± 22.68 | 17057.51 ± 407.77 | 12732.11 ± 981.42 |

TABLE IV-continued

Effect on Vascular Inflammation Markers

|  | N | MCP-1 (pg/mL) | CRP (ng/mL) | RBP-4 (ng/mL) | Leptin (pg/mL) | ICAM (pg/mL) | Adiponectin (ng/mL) |
|---|---|---|---|---|---|---|---|
| Cr(nic)$_2$Gly | 7 | 2897.61 ± 953.13 | 535.98 ± 21.20 | 54900.00 ± 3370.63 | 461.16 ± 63.69 | 16691.40 ± 361.13 | 12552.86 ± 961.72 |
| Niacin | 7 | 1365.66 ± 600.75 | 548.27 ± 23.65 | 53945.00 ± 3658.98 | 363.96 ± 15.37 | 16855.83 ± 386.02 | 8872.00 ± 479.48 |
| Cr(nic)$_2$Arg | 6 | 3235.62 ± 255.96 | 628.49 ± 14.76 | 52537.50 ± 891.06 | 335.80 ± 15.48 | 18591.76 ± 852.37 | 9279.38 ± 481.63 |
| Arg | 6 | 3878.85 ± 417.45 | 617.34 ± 29.21 | 47211.67 ± 2102.85 | 431.72 ± 46.39 | 17940.91 ± 474.12 | 9958.63 ± 176.77 |
| Cys | 6 | 2769.76 ± 222.75 | 551.39 ± 38.24 | 50915.00 ± 3416.90 | 477.65 ± 49.02 | 18512.88 ± 670.51 | 11532.37 ± 805.94 |
| CrNicGlyCysGlu | 6 | 2911.81 ± 174.07 | 564.10 ± 14.54 | 46577.78 ± 2215.22 | 361.11 ± 29.13 | 18621.43 ± 632.75 | 10152.28 ± 346.38 |
| CrHis | 6 | 2974.79 ± 862.09 | 710.26 ± 133.82 | 51112.60 ± 2856.20 | 436.96 ± 45.86 | — | 11455.87 ± 731.12 |
| CrProp | 6 | 4497.83 ± 547.42 | 820.04 ± 81.86 | 49851.91 ± 3664.21 | 393.47 ± 33.43 | — | 12903.52 ± 781.29 |
| Cr454 | 6 | 3232.18 ± 477.26 | 747.02 ± 60.39 | 48791.98 ± 2827.93 | 364.80 ± 54.52 | — | 11055.14 ± 201.42 |
| CrTrp | 7 | 2578.59 ± 388.46 | 609.82 ± 43.37 | 60593.24 ± 2972.93 | 601.72 ± 77.55 | — | 11122.93 ± 345.96 |
| CrCin | 7 | 2428.69 ± 329.03 | 587.35 ± 21.41 | 47905.13 ± 1751.73 | 379.18 ± 31.66 | — | 11507.60 ± 563.90 |
| Cr(5HTP)$_3$ | 7 | 1932.18 ± 280.81 | 589.26 ± 24.48 | 44517.99 ± 1550.87 | 359.61 ± 27.52 | — | 11831.51 ± 244.04 |
| Cr(nic)$_2$Gluc | 7 | 1977.46 ± 211.78 | 530.74 ± 22.37 | 48851.14 ± 2756.82 | 388.37 ± 56.16 | — | 11448.39 ± 412.77 |
| Cr(Phe)$_3$ | 7 | 2064.89 ± 211.78 | 533.12 ± 22.37 | 48555.98 ± 2756.82 | 387.92 ± 56.16 | — | 11243.47 ± 412.77 |

Each value represents the mean ± SE.

TABLE V

Effect on Other Vascular Inflammation Markers

|  | N | cAMP (pmol/mL) | TNFα (pg/mL) | IL-6 (pg/mL) | OxyDNA (ng/mL) |
|---|---|---|---|---|---|
| Baseline | 27 | 43.08 ± 3.26 | 26.53 ± 4.18 | 96.34 ± 1.57 | 55.96 ± 3.02 |
| Control | 25 | 30.21 ± 1.15 | 42.88 ± 10.05 | 91.59 ± 1.75 | 49.10 ± 1.52 |
| CrN | 20 | 32.29 ± 3.59 | 17.02 ± 3.59 | 91.42 ± 2.40 | 49.03 ± 1.56 |
| CrP | 19 | 29.17 ± 2.00 | 33.66 ± 5.27 | 94.13 ± 2.47 | 49.02 ± 2.31 |
| CrP + Biotin | 7 | 30.47 ± 2.41 | — | 91.05 ± 1.81 | 40.30 ± 2.35 |
| Cr(nic)$_2$Trp | 7 | 30.36 ± 1.48 | — | 92.09 ± 1.89 | 39.35 ± 3.48 |
| Cr(nic)$_2$Phe | 7 | 31.60 ± 1.22 | — | 84.82 ± 1.60 | 40.63 ± 3.74 |
| Cr(nic)$_2$Asp | 6 | 27.95 ± 1.22 | — | 88.91 ± 2.25 | 41.92 ± 1.46 |
| Cr(nic)$_2$Glu | 7 | 29.97 ± 1.43 | — | 89.50 ± 3.22 | 43.62 ± 2.69 |
| Cr(nic)$_2$Cys | 13 | 33.26 ± 2.61 | 17.72 ± 3.35 | 95.02 ± 1.99 | 46.92 ± 2.24 |
| Cr(nic)$_2$Gly | 7 | 31.40 ± 1.57 | — | 91.96 ± 3.83 | 45.62 ± 1.86 |
| Niacin | 7 | 34.27 ± 1.47 | — | 93.76 ± 1.60 | 47.31 ± 2.78 |
| Cr(nic)$_2$Arg | 6 | 38.96 ± 3.88 | 17.84 ± 1.26 | 92.35 ± 2.79 | 58.26 ± 2.57 |
| Arg | 6 | 34.98 ± 0.92 | 25.45 ± 0.93 | 97.80 ± 0.93 | 62.90 ± 2.71 |
| Cys | 6 | 32.94 ± 1.79 | 24.28 ± 3.84 | 95.33 ± 2.33 | 54.56 ± 5.69 |
| CrNicGlyCysGlu | 6 | 35.55 ± 0.89 | 23.37 ± 9.31 | 97.80 ± 1.42 | 56.07 ± 6.20 |
| CrHis | 6 | 28.07 ± 2.83 | 24.72 ± 5.24 | 91.98 ± 8.19 | 57.72 ± 2.86 |
| CrProp | 6 | 26.95 ± 1.13 | 41.14 ± 10.06 | 90.50 ± 14.02 | 47.19 ± 5.07 |
| Cr454 | 6 | 26.41 ± 3.20 | 20.69 ± 6.10 | 82.95 ± 5.25 | 46.57 ± 4.80 |
| CrTrp | 7 | 20.03 ± 0.96 | 36.61 ± 14.89 | 86.62 ± 6.81 | 45.14 ± 2.77 |
| CrCin | 7 | 29.24 ± 0.61 | 8.62 ± 4.90 | 92.94 ± 13.21 | 48.71 ± 1.25 |
| Cr(5HTP)$_3$ | 7 | 25.64 ± 2.39 | 13.35 ± 8.28 | 94.32 ± 11.71 | 45.89 ± 4.53 |
| Cr(nic)$_2$Gluc | 7 | 22.25 ± 1.58 | 29.40 ± 8.87 | 81.59 ± 5.21 | 45.10 ± 3.76 |
| Cr(Phe)$_3$ | 7 | 29.62 ± 1.01 | 15.92 ± 7.76 | 89.82 ± 8.55 | 53.11 ± 4.76 |

Each value represents the mean ± SE.

TABLE VI

Effect on Clinical Chemistry Abbreviations: AP:
Alkaline phosphatase; BUN: Blood Urea Nitrogen; CRT: Creatinine;
AST: Aspartate Aminotransferase; ALT: Alanine Aminotranserease.

| | N | AP (u/L) | BUN (mg/dL) | CRT (mg/dL) | AST (u/L) | ALT (u/L) | Total Bilirubin (mg/dL) | Anion Gap (μ/L) | BUN/CRT Ratio (mMol/L) |
|---|---|---|---|---|---|---|---|---|---|
| Baseline | 27 | 41.36 ± 6.01 | 14.74 ± 0.39 | 0.35 ± 0.01 | 271.83 ± 33.85 | 72.13 ± 1.72 | 0.07 ± 0.00 | 37.22 ± 0.91 | 43.17 ± 1.49 |
| Control | 25 | 55.86 ± 6.61 | 20.27 ± 0.64 | 0.43 ± 0.00 | 375.15 ± 90.35 | 244.09 ± 62.90 | 0.07 ± 0.01 | 28.77 ± 0.62 | 48.18 ± 1.93 |
| CrN | 20 | 45.39 ± 5.47 | 20.58 ± 1.10 | 0.43 ± 0.01 | 227.67 ± 33.31 | 133.53 ± 11.91 | 0.07 ± 0.01 | 28.00 ± 0.53 | 49.53 ± 2.96 |
| CrP | 19 | 40.06 ± 4.72 | 20.22 ± 1.09 | 0.41 ± 0.01 | 362.44 ± 51.87 | 179.78 ± 26.86 | 0.07 ± 0.01 | 29.61 ± 0.78 | 49.72 ± 2.57 |
| CrP + Biotin | 7 | 64.00 ± 5.78 | 19.14 ± 0.86 | 0.41 ± 0.01 | 160.29 ± 22.59 | 100.71 ± 10.08 | 0.10 ± 0.00 | 25.86 ± 1.16 | 46.50 ± 2.57 |
| Cr(nic)$_2$Trp | 7 | 61.43 ± 10.71 | 19.57 ± 1.04 | 0.40 ± 0.00 | 149.71 ± 28.07 | 89.29 ± 7.69 | 0.09 ± 0.01 | 27.14 ± 1.37 | 48.93 ± 2.61 |
| Cr(nic)$_2$Phe | 7 | 51.43 ± 8.25 | 19.71 ± 0.57 | 0.39 ± 0.01 | 135.29 ± 16.31 | 108.00 ± 10.52 | 0.10 ± 0.00 | 27.71 ± 0.78 | 51.43 ± 1.88 |
| Cr(nic)$_2$Asp | 6 | 53.00 ± 2.35 | 18.00 ± 0.84 | 0.42 ± 0.02 | 120.33 ± 17.89 | 96.00 ± 6.14 | 0.10 ± 0.00 | 26.00 ± 0.77 | 45.83 ± 1.90 |
| Cr(nic)2Glu | 7 | 52.86 ± 9.01 | 18.43 ± 0.69 | 0.41 ± 0.01 | 176.71 ± 23.22 | 105.57 ± 12.83 | 0.10 ± 0.00 | 27.00 ± 1.38 | 44.71 ± 2.03 |
| Cr(nic)$_2$Cys | 13 | 35.15 ± 3.95 | 18.23 ± 0.64 | 0.41 ± 0.00 | 261.17 ± 41.43 | 99.00 ± 6.03 | 0.05 ± 0.01 | 29.62 ± 0.58 | 44.92 ± 1.70 |
| Cr(nic)$_2$Gly | 7 | 40.50 ± 3.53 | 16.71 ± 0.47 | 0.40 ± 0.00 | 176.71 ± 23.22 | 90.83 ± 3.46 | 0.10 ± 0.00 | 29.43 ± 1.04 | 41.07 ± 1.53 |
| Niacin | 7 | 46.50 ± 8.01 | 19.33 ± 0.84 | 0.40 ± 0.00 | 261.17 ± 41.43 | 126.17 ± 15.74 | 0.10 ± 0.00 | 28.67 ± 0.84 | 48.33 ± 2.11 |
| Cr(nic)$_2$Arg | 6 | 40.20 ± 5.96 | 20.00 ± 0.68 | 0.42 ± 0.02 | 241.50 ± 29.34 | 147.33 ± 24.54 | 0.00 ± 0.00 | 27.60 ± 0.51 | 48.33 ± 2.09 |
| Arg | 6 | 35.50 ± 7.98 | 21.00 ± 0.45 | 0.40 ± 0.00 | 276.80 ± 48.90 | 179.20 ± 23.91 | 0.00 ± 0.00 | 27.75 ± 0.85 | 52.60 ± 1.12 |
| Cys | 6 | 36.40 ± 4.65 | 18.50 ± 0.29 | 0.42 ± 0.02 | 218.20 ± 25.46 | 119.20 ± 11.37 | 0.00 ± 0.00 | 29.20 ± 0.49 | 43.00 ± 2.53 |
| CrNicGlyCysGlu | 6 | 36.16 ± 8.33 | 19.33 ± 1.05 | 0.40 ± 0.00 | 241.17 ± 50.71 | 160.00 ± 39.72 | 0.00 ± 0.00 | 28.33 ± 0.67 | 48.67 ± 2.55 |
| CrHis | 6 | 35.25 ± 11.52 | 19.50 ± 0.50 | 0.40 ± 0.00 | 248.00 ± 19.22 | 168.25 ± 22.41 | 0.10 ± 0.00 | 29.75 ± 1.32 | 48.75 ± 1.25 |
| CrProp | 6 | 32.20 ± 10.68 | 22.25 ± 0.48 | 0.40 ± 0.00 | 347.25 ± 50.92 | 207.00 ± 49.00 | 0.10 ± 0.00 | 29.20 ± 0.97 | 53.40 ± 2.77 |
| Cr454 | 6 | 31.50 ± 10.38 | 20.00 ± 1.15 | 0.38 ± 0.02 | 439.50 ± 90.07 | 213.67 ± 51.00 | 0.10 ± 0.00 | 30.00 ± 1.55 | 48.80 ± 3.1209 |
| CrTrp | 7 | 30.00 ± 7.79 | 17.43 ± 0.61 | 0.39 ± 0.01 | 237.43 ± 55.49 | 124.29 ± 16.77 | 0.10 ± 0.00 | 30.14 ± 0.34 | 45.86 ± 2.82 |
| CrCin | 7 | 30.71 ± 6.82 | 21.43 ± 1.38 | 0.41 ± 0.01 | 230.14 ± 20.78 | 158.71 ± 23.76 | 0.10 ± 0.00 | 29.86 ± 0.26 | 51.86 ± 1.72 |
| Cr(5HTP)$_3$ | 7 | 25.00 ± 8.28 | 22.86 ± 1.39 | 0.40 ± 0.00 | 267.43 ± 22.84 | 167.00 ± 25.31 | 0.10 ± 0.00 | 29.43 ± 0.53 | 57.29 ± 3.42 |
| Cr(nic)$_2$Gluc | 7 | 27.00 ± 8.53 | 21.33 ± 0.84 | 0.40 ± 0.00 | 238.67 ± 25.03 | 138.00 ± 12.83 | 0.10 ± 0.00 | 29.00 ± 1.03 | 53.67 ± 2.12 |
| Cr(Phe)3 | 7 | 30.00 ± 7.65 | 20.71 ± 1.08 | 0.40 ± 0.00 | 276.43 ± 48.30 | 186.29 ± 39.13 | 0.10 ± 0.00 | 29.00 ± 0.52 | 52.14 ± 2.73 |

Each value represents the mean ± SE

The foregoing description is given for clearness of understanding only, and no unnecessary limitations should be understood therefrom, as modifications within the scope of the invention may be apparent to those having ordinary skill in the art.

What is claimed is:

1. A method for treating diabetes, the method comprising administering a biologically effective amount of a composition comprising an isolated and purified complex of trivalent chromium dinicocysteinate to a subject in need thereof.

2. The method of claim 1, wherein the biologically effective amount increases vitamin C levels.

3. The method of claim 1, wherein the biologically effective amount comprises about 10 μg to about 1000 μg of elemental chromium.

4. The method of claim 1, wherein the composition is administered daily.

5. The method of claim 1, wherein the biologically effective amount comprises about 400 μg of elemental chromium.

6. The method of claim 1, wherein the subject is a mammal.

7. The method of claim 6, wherein the mammal is human.

8. The method of claim 6, wherein the mammal is a swine.

9. The method of claim 1, wherein the subject is avian.

10. A method for treating symptoms associated with diabetes or with the onset of diabetes, the method comprising administering a biologically effective amount of a composition comprising an isolated and purified complex of trivalent chromium dinicocysteinate to a subject suffering from symptoms associated with diabetes or with the onset of diabetes.

11. The method of claim 10, wherein symptoms associated with diabetes or with the onset of diabetes are treated by lowering the blood levels of one or more of fasting glucose, glycosylated hemoglobin, monocyte chemotactic protein-1, intracellular adhesion molecule, and red blood cell lipid peroxidase.

12. The method of claim 10, wherein symptoms associated with diabetes or with the onset of diabetes are treated by increasing the blood levels of one or both of vitamin C and adiponectin.

13. A method for treating symptoms associated with atherosclerosis, the method comprising administering a biologically effective amount of a composition comprising an isolated and purified complex of trivalent chromium dinicocysteinate to a subject suffering from atherosclerosis.

14. A method for treating symptoms associated with cardiovascular disease, the method comprising administering a biologically effective amount of a composition comprising an isolated and purified complex of trivalent chromium dinicocysteinate to a subject suffering from symptoms associated with cardiovascular disease.

15. The method of claim 14, wherein symptoms associated with cardiovascular disease are treated by lowering elevated LDL cholesterol, VLDL cholesterol, triglycerides, C-reactive protein, blood pressure and/or vascular inflammation levels, and/or increasing HDL cholesterol levels.

* * * * *